US009734512B2

(12) United States Patent
Alhimiri

(10) Patent No.: US 9,734,512 B2
(45) Date of Patent: Aug. 15, 2017

(54) RATING SYSTEM, PROCESS AND ALGORITHMIC BASED MEDIUM FOR TREATMENT OF MEDICAL CONDITIONS IN COST EFFECTIVE FASHION UTILIZING BEST TREATMENT PROTOCOLS AND FINANCIAL ASSESSMENT TOOLS FOR DETERMINING A MAXIMUM CUTOFF POINT FOR ASSESSING HEALTHCARE RETURN ON INVESTMENT AND TO PROVIDE FOR IMPROVED CLINICAL/FUNCTIONAL OUTCOMES

(71) Applicant: Ali Alhimiri, Allen Park, MI (US)

(72) Inventor: Ali Alhimiri, Allen Park, MI (US)

( * ) Notice: Subject to any disclaimer, the term of this patent is extended or adjusted under 35 U.S.C. 154(b) by 352 days.

(21) Appl. No.: 14/495,378

(22) Filed: Sep. 24, 2014

(65) Prior Publication Data
US 2015/0088628 A1 Mar. 26, 2015

Related U.S. Application Data

(60) Provisional application No. 61/883,004, filed on Sep. 26, 2013.

(51) Int. Cl.
*G06Q 30/02* (2012.01)
(52) U.S. Cl.
CPC .............................. *G06Q 30/0217* (2013.01)
(58) Field of Classification Search
CPC ................................................ G06Q 30/0217
(Continued)

(56) References Cited

U.S. PATENT DOCUMENTS 2,647,727 A  8/1953  Edwards
4,645,006 A  2/1987  Tinsley
(Continued)

FOREIGN PATENT DOCUMENTS

CN  102654890 A  9/2012
CN  102947857 A  2/2013
(Continued)

OTHER PUBLICATIONS

Microsoft Computer Dictionary, Fifth Edition, 2002, Microsoft Press, p. 23.*
(Continued)

*Primary Examiner* — Namrata Boveja
*Assistant Examiner* — Michael Ezewoko
(74) *Attorney, Agent, or Firm* — Dinsmore & Shohl LLP

(57) ABSTRACT

The present invention discloses a system, method and non-transitory software based computer writeable medium usable with a processor driven device for incentivizing service providers. A first subroutine assembles a best practices model in the form of a database downloadable to the processor device and which presents series of treatment options ranging from desirable to undesirable associated with a given type of service. A second subroutine provides a decision support system interfacing with the best practices database and processor device, the support system providing any of a grading or awarding system for scoring, in real time, performance metrics for each of any number of providers of the service. A third subroutine outputs to each of the providers, real time and continuously updated scoring of their performance metrics based upon the grading/awarding system. A fourth subroutine for incentivizing adherence by the providers to the best practices model by tying desirable performance metrics to financial incentives which are scaled to each treatment option.

17 Claims, 17 Drawing Sheets

(58) Field of Classification Search
USPC .................................................. 705/14.19
See application file for complete search history.

(56) References Cited

U.S. PATENT DOCUMENTS

| | | | |
|---|---|---|---|
| 6,253,861 | B1 | 7/2001 | Carmichael et al. |
| 6,732,793 | B1 | 5/2004 | Lee |
| 6,820,697 | B1 | 11/2004 | Churchill |
| 7,055,605 | B2 | 6/2006 | Howlett et al. |
| 7,347,288 | B2 | 3/2008 | Lee |
| 7,347,289 | B2 | 3/2008 | Lee |
| 7,387,165 | B2 | 6/2008 | Lopez de Cardenas et al. |
| 7,395,216 | B2 | 7/2008 | Rosenfeld et al. |
| 7,416,029 | B2 | 8/2008 | Telfer et al. |
| 7,693,727 | B2 | 4/2010 | Moore |
| 7,925,519 | B2 * | 4/2011 | Greene .............. G06F 19/328 705/2 |
| 8,086,471 | B2 | 12/2011 | Gamboa et al. |
| 8,117,047 | B1 | 2/2012 | Cusimano-Reaston et al. |
| 8,489,412 | B1 | 7/2013 | Gliklich |
| 8,645,166 | B2 * | 2/2014 | Bessette .............. A61B 5/00 705/2 |
| 2004/0044546 | A1 | 3/2004 | Moore |
| 2006/0025931 | A1 | 2/2006 | Rosen et al. |
| 2008/0114618 | A1 | 5/2008 | Pysnik et al. |
| 2008/0114689 | A1 | 5/2008 | Psynik et al. |
| 2012/0109689 | A1 | 5/2012 | Lee |
| 2012/0284052 | A1 | 11/2012 | Saukas et al. |
| 2013/0117033 | A1 | 5/2013 | Mohlenbrock |
| 2013/0151281 | A1 | 6/2013 | Kaburick et al. |
| 2013/0159023 | A1 | 6/2013 | Srinivas et al. |
| 2014/0108030 | A1 * | 4/2014 | Tejeda-Monteagut G06F 19/327 705/2 |
| 2014/0136233 | A1 | 5/2014 | Atkinson et al. |
| 2015/0088628 | A1 | 3/2015 | Alhimiri |

FOREIGN PATENT DOCUMENTS

| | | |
|---|---|---|
| JP | 10021298 A | 1/1998 |
| WO | 2004022907 A1 | 3/2004 |
| WO | 2004088091 A1 | 10/2004 |
| WO | 2004106694 A1 | 12/2004 |

OTHER PUBLICATIONS

Mind—A Brief Introduction, John R. Searle, 2004, Oxford University Press, pp. 62-67.*
What is Thought, Eric Baum, The MIT Press, 2004, pp. 33-65.*
Robotics, Science and Systems III, Wolfram Burgard, Oliver Brock, and Cyrill Stachniss, The MIT Press, 2008, pp. 41-48.*
Language and Mind, Chomsky, Oxford University Press, 2005, p. 62.*
Computing the Mind, Shimon Edelman, Oxford University Press, 2008, pp. 26-31.*
Noetics, Lawrence Krader, 2010, Peter Lang Publishing, pp. 551-553.*
Britannica Concise Encyclopedia, Encyclopedia Britannica, 2006, p. 537.*
Mafi et al., Worsening trends in the management and treatment of back pain, JAMA Internal Medicine, Sep. 23, 2013, 1573-1581, 173(17), doi: 10.1001/jamainternmed.2013.8992, Retrieved from http://archinte.jamanetwork.com/article.aspx?articleid=1722522.
International Search Report and Written Opinion of the International Searching Authority, dated Oct. 28, 2016.
Harvard Business Review, The Employer-Led Health Care Revolution by Patricia A. McDonald, Robert S. Mecklenburg, and Lindsay A. Martin, from the Jul.-Aug. 2015 Issue, 25 pages Publication Date: Jul. 1, 2015.

* cited by examiner

FIG. 4

ACO/SC Spine Program

| Metric/Year | SC percentile % Best Practice more> better | Value factor | % Best Practice index | SC Delta change in Functional Outcome disability rate less> better | Value factor | Functional Outcome disability rate index | SC Patient Satisfaction more> better | Value factor | Patient Satisfaction index | ACO $ Cost per all patient PMPM less> better | ACO $ Cost per spine patient PMPM less> better | ACO $ Cost average PMPM less> better | Value factor | $/Patient index | Total Index per provider (should be less than 1) | 50/50 split PCP and non-PCP providers | Year end Savings |
|---|---|---|---|---|---|---|---|---|---|---|---|---|---|---|---|---|---|
| Providers | | | | | | | | | | | | | | | PCP minimum compliance rate for any saved savings is 80% (0.8) | | 300000 |
| PCPs | Fill out | | Fill out | Fill out | | | Fill out | | | | | Fill out | | | | | |
| AA | 95 | 0.5 | 0.5 | 10 | 0.2 | 0.2 | 80 | 0.1 | 0.1 | 20 | 8 | 14 | 0.2 | 0.2 | 1 | 10655 | |
| BB | 100 | 0.5 | 0.475 | 10 | 0.2 | 0.18 | 80 | 0.1 | 0.08 | 20 | 8 | 14 | 0.2 | 0.1972 | 0.9322 | 9932.7 | |
| CC | 98 | 0.5 | 0.5 | 40 | 0.2 | 0.12 | 75 | 0.1 | 0.075 | 30 | 3 | 16.5 | 0.2 | 0.1967 | 0.8917 | 9501.1 | |
| DD | 99 | 0.5 | 0.49 | 10 | 0.2 | 0.18 | 60 | 0.1 | 0.06 | 10 | 5 | 7.5 | 0.2 | 0.1985 | 0.9285 | 9893.2 | |
| EE | 99 | 0.5 | 0.495 | 40 | 0.2 | 0.12 | 90 | 0.1 | 0.09 | 8 | 12 | 10 | 0.2 | 0.198 | 0.903 | 9621.5 | |
| FF | 96 | 0.5 | 0.48 | 20 | 0.2 | 0.16 | 95 | 0.1 | 0.095 | 24 | 8 | 16 | 0.2 | 0.1968 | 0.9318 | 9928.4 | |
| GG | 99 | 0.5 | 0.495 | 10 | 0.2 | 0.18 | 65 | 0.1 | 0.065 | 19 | 10 | 14.5 | 0.2 | 0.1971 | 0.9371 | 9984.9 | |
| HH | 95 | 0.5 | 0.475 | 20 | 0.2 | 0.16 | 40 | 0.1 | 0.04 | 21 | 11 | 16 | 0.2 | 0.1968 | 0.8718 | 9289.1 | |
| II | 97 | 0.5 | 0.485 | 50 | 0.2 | 0.1 | 20 | 0.1 | 0.02 | 20 | 16 | 18 | 0.2 | 0.1964 | 0.8014 | 8539.0 | |
| JJ | 50 | 0.5 | 0.25 | 30 | 0.2 | 0.14 | 80 | 0.1 | 0.08 | 22 | 5 | 13.5 | 0.2 | 0.1973 | | 0.0 | |
| KK | 97 | 0.5 | 0.485 | 50 | 0.2 | 0.1 | 30 | 0.1 | 0.03 | 26 | 3 | 14.5 | 0.2 | 0.1971 | 0.8121 | 8653.0 | |
| LL | 98 | 0.5 | 0.49 | 60 | 0.2 | 0.08 | 50 | 0.1 | 0.05 | 18 | 2 | 10 | 0.2 | 0.198 | 0.818 | 8715.9 | |
| MM | 100 | 0.5 | 0.5 | 20 | 0.2 | 0.16 | 40 | 0.1 | 0.04 | 23 | 4 | 13.5 | 0.2 | 0.1973 | 0.8973 | 9560.8 | |
| NN | 100 | 0.5 | 0.5 | 10 | 0.2 | 0.18 | 20 | 0.1 | 0.02 | 23 | 6 | 14.5 | 0.2 | 0.1971 | 0.8971 | 9558.7 | |
| OO | 99 | 0.5 | 0.495 | 50 | 0.2 | .01 | 70 | 0.1 | 0.07 | 17 | 5 | 11 | 0.2 | 0.1978 | 0.8628 | 9193.2 | |
| PP | 60 | 0.5 | 0.3 | 10 | 0.2 | 0.18 | 80 | 0.1 | 0.08 | 12 | 9 | 10.5 | 0.2 | 0.1979 | | 0.0 | |
| QQ | 72 | 0.5 | 0.36 | 30 | 0.2 | 0.14 | 70 | 0.1 | 0.07 | 10 | 11 | 10.5 | 0.2 | 0.1979 | | 0.0 | |
| RR | 98 | 0.5 | 0.49 | 20 | 0.2 | 0.16 | 20 | 0.1 | 0.02 | 22 | 13 | 17.5 | 0.2 | 0.1965 | 0.8665 | 9232.6 | |
| SS | 99 | 0.5 | 0.495 | 30 | 0.2 | 0.14 | 40 | 0.1 | 0.04 | 13 | 6 | 9.5 | 0.2 | 0.1981 | 0.8731 | 9302.9 | |
| TT | 95 | 0.5 | 0.475 | 20 | 0.2 | 0.16 | 20 | 0.1 | 0.02 | 12 | 4 | 8 | 0.2 | 0.1984 | 0.8534 | 9093.0 | |
| UU | 60 | 0.5 | 0.3 | 0 | 0.2 | 0.2 | 40 | 0.1 | 0.04 | 10 | 3 | 6.5 | 0.2 | 0.1987 | | 0.0 | |
| Total PCPs | | | | | | | | | | | | | | | 14.0778 | | |
| | | | | | | | | | | | | | | Units | 150000 | 150000.0 | |
| | | | | | | | | | | | | | | $ share | 10655.07395 | | |
| | | | | | | | | | | | | | | $/unit | | | |

| Metric/Year | MODUS % Best Practice more> better | Value factor | % Best Practice Index | MODUS Functional Outcome Score | Value factor | Functional Outcome disability rate index | MODUS Patient Satsfaction more> better | Value factor | Patient Satsfaction index | Payers' Cost Score | Value factor | $/Patient Index | Total Index per provider (should be less than 1) | Total Provider Year end Savings Available | Shared Savings 50/50 Split between PCP & Specialist | Shared #1,2,3,4,5,6,7, 8,9,10,12,13,15, 16 |
|---|---|---|---|---|---|---|---|---|---|---|---|---|---|---|---|---|
| Providers | | | | | | | | | | | | | | | | |
| PCPs | Fill out | 0.3 | 0.3 | Fill out | 0.3 | 0.3 | Fill out | 0.1 | 0.1 | Fill out | 0.3 | 0.3 | 1 | 300000 | | |
| AA | 95 | 0.3 | 0.285 | 70 | 0.3 | 0.09 | 80 | 0.1 | 0.08 | 50 | 0.3 | 0.285 | 0.74 | | $7,903 | |
| BB | 100 | 0.3 | 0.3 | 60 | 0.3 | 0.12 | 75 | 0.1 | 0.075 | 65 | 0.3 | 0.2805 | 0.7755 | | $8,282 | |
| CC | 98 | 0.3 | 0.294 | 40 | 0.3 | 0.18 | 60 | 0.1 | 0.06 | 50 | 0.3 | 0.285 | 0.819 | | $8,747 | |
| DD | 99 | 0.3 | 0.297 | 30 | 0.3 | 0.21 | 90 | 0.1 | 0.09 | 0 | 0.3 | 0.3 | 0.897 | | $9,580 | |
| EE | 96 | 0.3 | 0.288 | 65 | 0.3 | 0.105 | 95 | 0.1 | 0.095 | 65 | 0.3 | 0.2805 | 0.7685 | | $8,208 | |
| FF | 99 | 0.3 | 0.297 | 68 | 0.3 | 0.096 | 65 | 0.1 | 0.065 | 15 | 0.3 | 0.2955 | 0.7535 | | $8,047 | |
| GG | 95 | 0.3 | 0.285 | 72 | 0.3 | 0.084 | 40 | 0.1 | 0.04 | 0 | 0.3 | 0.3 | 0.709 | | $7,572 | |
| HH | 97 | 0.3 | 0.291 | 85 | 0.3 | 0.045 | 20 | 0.1 | 0.02 | 50 | 0.3 | 0.285 | 0.641 | | $6,846 | |
| JJ | 97 | 0.3 | 0.291 | 69 | 0.3 | 0.093 | 30 | 0.1 | 0.03 | 65 | 0.3 | 0.2805 | 0.6945 | | $7,417 | |
| SS | 95 | 0.3 | 0.285 | 86 | 0.3 | 0.042 | 20 | 0.1 | 0.02 | 65 | 0.3 | 0.2805 | 0.6275 | | $6,702 | |
| TT | 28 | 0.3 | 0.084 | 32 | 0.3 | 0.204 | 70 | 0.1 | 0.07 | 65 | 0.3 | 0.2805 | 0.6385 | | $6,819 | |
| PMR | | | | | | | | | | | | | | | | |
| PMR1 | 95 | 0.3 | 0.0285 | 75 | 0.3 | 0.075 | 90 | 0.1 | 0.09 | 65 | 0.3 | 0.2805 | 0.474 | | $16,843 | |
| PMR2 | 100 | 0.3 | 0.03 | 83 | 0.3 | 0.051 | 85 | 0.1 | 0.085 | 15 | 0.3 | 0.2955 | 0.462 | | $16,399 | |
| Spine Surgeon | | | | | | | | | | | | | | | | |
| SS1 | 100 | 0.3 | 0.03 | 68 | 0.3 | 0.096 | 80 | 0.1 | 0.08 | 65 | 0.3 | 0.2805 | 0.487 | | $17,287 | |
| Chiropractor | | | | | | | | | | | | | | | | |
| Chiro1 | | 0 | 0 | 75 | 0.3 | 0.075 | 75 | 0.1 | 0.075 | 65 | 0.3 | 0.2805 | 0.431 | | $15,297 | |
| Psychology | | | | | | | | | | | | | | | | |
| Psy1 | | 0 | 0 | 65 | 0.3 | 0.105 | 80 | 0.1 | 0.08 | 65 | 0.3 | 0.2805 | 0.466 | | $16,541 | |
| Physical Therapy | | | | | | | | | | | | | | | | |
| PT1 | | 0 | 0 | 80 | 0.3 | 0.06 | 75 | 0.1 | 0.075 | 50 | 0.3 | 0.285 | 0.420 | | $14,924 | |
| PT2 | | 0 | 0 | 70 | 0.3 | 0.1 | 90 | 0.1 | 0.09 | 15 | 0.3 | 0.2955 | 0.476 | | $16,896 | |
| PT3 | | 0 | 0 | 65 | 0.3 | 0.1 | 91 | 0.1 | 0.091 | 65 | 0.3 | 0.2805 | 0.477 | | $16,932 | |

102

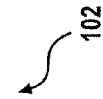

FIG. 7

Enroll Patient

Q (physician ▸)

16

Please complete the following information to enroll a patient into the CVI system.

- first name (Jack)
- last name (Payne)
- last 4 digits ssn
- birthdate ▸
- gender ▸
- ethnicity ▸
- primary language ▸
- marital status ▸
- address 1

Jack Payne's Recommendations
for their visit on 08/20/2014 at 6:10 PM.

Review of System for Spine Pain Report

Positive Responses

None

Negative Responses

Fever or Chills, Nightsweat, Headaches, History of Cancer, Recent Trauma, Recent Infection, Unintentional Weight Loss, Unintentional Weight Gain, Neck Pain, Back Pain, Joint or Limb Pain, Limited Range of Motion, Stiffness, Swelling, Numbness of Tingling, Loss of or Changed Sensation, Bladder of Bowel Problems, Localized Weakness, Impaired Balance, Tripping of Falling, Loss of Coordination, Paralysis, Stress of Any Kind, Anxiety or Depression, Disturbed Sleep, Blood in Urine. Blood in Stool, Abdominal Pain, Other Symptoms,

5,8,10,11, 12,14

130 ⟶ ⚑ ⚑ ⚑ ⚑

Management

A purple flag indicates impaired patient function. It is recommended that a referral should be made to a PMR and that the patient be treated in your office using the options below.

Make A Referral

☑ PMR          ☐ Specialist

[ End Visit ]

Best Practice

Compliant — 132

Functional Score

Jack Payne's Recommendations
for their visit on 08/20/2014 at 3:41 PM.

Review of System for Spine Pain Report

Positive Responses
None

Negative Responses
Fever or Chills, Nightsweat, Headaches, History of Cancer, Recent Trauma, Recent Infection, Unintentional Weight Loss, Unintentional Weight Gain, Neck Pain, Back Pain, Joint or Limb Pain, Limited Range of Motion, Stiffness, Swelling, Numbness of Tingling, Loss of or Changed Sensation, Bladder of Bowel Problems, Localized Weakness, Impaired Balance, Tripping of Falling, Loss of Coordination, Paralysis, Stress of Any Kind, Anxiety or Depression, Disturbed Sleep, Blood in Urine, Blood in Stool, Abdominal Pain, Other Symptoms,

5,8,10,11, 12,14

146 → 148

Management
A yellow flag indicates an increase in the patient's anxiety level. It is recommended that a referral should be made to a PMR and that the patient be treated in your office using the options below.

Make A Referral
■ PMR     □ Specialist
150

Best Practice — End Visit
Compliant — 132
Functional Score

Jack Payne's Recommendations
for their visit on 08/20/2014 at 6:14 PM.

Review of System for Spine Pain Report

Positive Responses
None

Negative Responses
Fever or Chills, Nightsweat, Headaches, History of Cancer, Recent Trauma, Recent Infection, Unintentional Weight Loss, Unintentional Weight Gain, Neck Pain, Back Pain, Joint or Limb Pain, Limited Range of Motion, Stiffness, Swelling, Numbness of Tingling, Loss of or Changed Sensation, Bladder of Bowel Problems, Localized Weakness, Impaired Balance, Tripping of Falling, Loss of Coordination, Paralysis, Stress of Any Kind, Anxiety or Depression, Disturbed Sleep, Blood in Urine, Blood in Stool, Abdominal Pain, Other Symptoms,

5,8,10,11,
12,14

Management

A red flag has been raised. It is recommended that a referral should be made.

A red flag may also indicate an emergency. Can the patient wait for 2 business days?

◉ Yes   ○ No

Suspected Diagnosis: ▽

164

166

End Visit

Best Practice

Compliant

Functional Score

RATING SYSTEM, PROCESS AND ALGORITHMIC BASED MEDIUM FOR TREATMENT OF MEDICAL CONDITIONS IN COST EFFECTIVE FASHION UTILIZING BEST TREATMENT PROTOCOLS AND FINANCIAL ASSESSMENT TOOLS FOR DETERMINING A MAXIMUM CUTOFF POINT FOR ASSESSING HEALTHCARE RETURN ON INVESTMENT AND TO PROVIDE FOR IMPROVED CLINICAL/FUNCTIONAL OUTCOMES

CROSS REFERENCE TO RELATED APPLICATIONS

The present application claims the priority of U.S. Ser. No. 61/883,004 filed Sep. 26, 2013, the contents of which is incorporated herein in its entirety.

BACKGROUND OF THE INVENTION

Field of the Invention

The present invention is generally directed to financial-bio-psycho social management models for optimal treatment of a chronic medical conditions, such as in one non-limiting instance being directed to achieving uncomplicated spinal pain management. More particularly, the present invention discloses a system, process and algorithmic based non-transitory computer writeable medium for incorporating best practices protocols into a multi-faceted module for treating a variety of medical conditions (including spinal pain management, heart disease, various types of cancers, etc.). Desired objectives of the system include each of adherence to best practices, patient functional outcome and patient satisfaction, the objective of which being to maximize economy of medical expense while recognizing and appropriately compensating medical providers for value received. In this way, the present invention attempts to improve upon the existing business model for medical care by incentivizing quality of care and resultant patient outcome, as opposed to basing compensation primarily upon the volume of care provided (such including test, medical procedures, etc.).

The present system seeks to revolutionize health care by implementing best care protocols, these established by the relevant payer or ACO (accountable care organization). The system provides financial incentivizes for the individual provider (e.g. MD or other professional) to adhere to the established protocols, this in large part dictated by the ACO establishing compensation in large part as a variable of the provider's adherence to the established best care protocols (as reflected in a given provider's score card), the effect of which being to improve the value of the physician patient relationship with better health outcomes achieved at lower cost. Additional advantages include providing clinical providers groups with clinical insight, leadership, education and training for management. The present system, method and software based algorithmic medium further serves to return the lost value to the patient/physician relationship.

Description of the Background Art

The prior art is documented with examples of systems and methods, such as utilized in the medical field. A first example of this is set forth in Moore, U.S. Pat. No. 7,693,727 which teaches interactive systems and methods for directing, integrating, documenting, and tracking steps taken by medical providers during the process of care for a patient's given condition. Doctors' actions are directed by a prescriptive protocol—a checklist of discrete steps designed for efficient or optimal care of an individual patient's specific condition. The step-by-step checklist is abstracted from decision tree guidelines for the optimal work up and treatment for the condition using probability-based methodology. The care protocols can be derived from widely available and non-proprietary guidelines and decision trees based on public medical research literature.

In one embodiment, the invention can be employed by a primary care clinician at the point of referral into the specialist sector, and at the specialist level when proposing a risky or expensive or otherwise problematic medical or surgical diagnostic or treatment intervention. At these two critical transaction points in care, the checklist functions like a lock, based on a hidden clinical decision algorithm (an explanation of which can be displayed upon request). The system asks the clinician for data and then generates the patient's optimal checklist, displaying it as a point and click form keyed to the stage of care being undertaken by each doctor. As the clinician enters data into the checklist, a decision engine determines whether the checklist data satisfies predetermined criteria for authorization of the proposed action. The system can also document each transaction taken in the process of care to create an electronic record that can be made accessible to all clinicians involved in the process of care.

Moore, US 2004/0044546 teaches interactive methods and systems for directing, integrating, documenting and tracking steps taken by medical providers during the process of care for a given patient's condition. Doctors' actions are directed by a prescriptive protocol—a checklist of discrete steps designed for efficient or optimal care of an individual patient's specific condition. The step-by-step checklist is abstracted from decision tree guidelines for the optimal work up and treatment for the condition using probability-based methodology. The care protocols can be derived from widely available and non-proprietary guidelines and decision trees based on public medical research literature.

In one embodiment, the invention can be employed by a primary care clinician at the point of referral into the specialist sector, and at the specialist level when proposing a risky or expensive or otherwise problematic medical or surgical diagnostic or treatment intervention. At these two critical transaction points in care, the checklist functions like a lock, based on a hidden clinical decision algorithm (an explanation of which can be displayed upon request). The system asks the clinician for data and then generates the patients optimal checklist, displaying it as a point and click form keyed to the stage of care being undertaken by each doctor. As the clinician enters data into the checklist, a decision engine determines whether the checklist data satisfies predetermined criteria for authorization of the proposed action. The system can also document each transaction taken in the process of care to create an electronic record that can be made accessible to all clinicians involved in the process of care.

A further example of the prior art is the healthcare providing organization (HPO) model of Cusimano-Reaston et al., U.S. Pat. No. 8,117,047, and which teaches a preferred provider network (PPO) or other membership agreement that allows individuals or groups to join via a membership contract. The contract allows the HPO to provide a technical component of a medical evaluation or service. Additionally, the HPO employs or retains the services of healthcare professionals who participate in and monitor an evaluation of a patient who can be at a remote location from the healthcare professional. The HPO provides a medical diagnostic unit, which is known as an EFA-2, that allows the healthcare professional to receive data that pertains to the patient via a real-time communication protocol, or the patient data is collected and stored on an electronic storage device. The healthcare professional then analyzes the patient data and issues recommended treatment.

Lee, US 2012/0109689 teaches a support system for improved quality healthcare, defined as MEGICS (Medical+ Logistics), developed in order to improve quality of care and enhance the efficiency of operation of healthcare facilities and providers. When front-line healthcare doctors and nurses make various clinical decisions, MEGICS management system provides them with relevant clinical knowledge in a timely manner with the stated objective being to increase user satisfaction and provide better quality of healthcare services.

Gliklich, U.S. Pat. No. 8,489,412, teaches a data processing system for determining clinical outcomes of medical data gathered by the system. A doctor defines a medical study and can administer and collect data relevant to that study in real time from potentially geographically diverse doctors, patients and other people associated with the study. The system can analyze the medical data in real-time according to any number of clinical algorithms that may be custom defined and edited before and during the study. The clinical algorithms produce clinical outcome data that can be used for treatment of patients participating in the study immediately after the data is input and analyzed. The medical outcomes can indicate such things as performance comparisons, composite outcomes, and risk stratification and assessments for such things as treatments, drugs, illnesses, doctors, patients and physicians groups.

In summary, and while describing various systems, methods and protocols for attempting to optimize the efficiency of patient care, the prior art as a generalization acknowledges the inviolability of the present healthcare delivery model with its existing compensation and incentive structures. These notably reward physicians and other medical providers based on the quantum of care provided (e.g. tests conducted, surgical procedures performed, etc.) and as opposed to tying such compensation/incentives to documentable patient outcomes.

SUMMARY OF THE PRESENT INVENTION

The present invention provides a system, method and non-transitory and software/algorithmic based computer writeable medium for revolutionizing the delivery of healthcare, this primarily through the formulation and implementation of results driven compensation/incentives to the provider (e.g. doctor, surgeon or other medical care professional), and as opposed to traditional compensation methods which reward such providers on the basis of quantum of care provided (tests ordered, surgical procedures conducted). The underpinnings of the present invention include a central processor into which is loaded a best practices and corresponding (financial) incentive database, the contents of which can be promulgated or modified by a given payor or ACO (accountable care organization).

A patient kiosk (such loosely defined to include any patient accessible input ranging from a physical station to a mobile application loaded into a smartphone or tablet computer) and which permits a patient to input necessary biographical and medically relevant information along with other information, the carrot for providing which can include additional benefits and enticements. A decision support system interfaces with the processor and, in combination with additional information inputs required by the service provider (e.g. physician, group of physicians or other designated care providing entity including a hospital, clinic, etc.) formulates a provider scorecard for each such individual or entity which grades and rewards such providers based upon their adherence to the best practice standards set by the ACO or other payor.

In this fashion, the present invention seeks to recalibrate the incentive structure of the care provider (such as further defined in non-limiting fashion to include healthcare facilities such as hospitals and nursing homes and in addition to individual physicians or various general/specialized practice groups) by, in large part, tying compensation to adherence to the best practices standards and protocols set by the local ACO or other responsible payor. In this fashion, and by delegating responsibility for the formulation, administration and enforcement of the present system to the designated (e.g. local) payor/ACO, the various care providers are generally are understood to accede to these established standards and protocols, thereby providing the necessary participation for guaranteeing the success of the model.

The advantage of this system is that it rewards/compensates such care providers based upon the desired outcome of treatment which is in accordance with the established practices and protocols (quality of treatment), and without regards to the quantum of treatment provided (number of tests ordered, surgical procedures performed, etc.). At the same time, such care providers are rewarded for any level or quantity of treatment (again including tests, procedures, etc.) which are consistent with the desired standards established by the ACO and, equally importantly, are provided according to the protocols established. One application of this is to incentivize the care provider to follow the desired practices and protocols first and before resorting immediately to invasive medical procedures which do not contribute to overall patient quality of care so much as to the financial benefit of the care provider. Beyond physician and physician groups, the present inventions are further understood to apply to all clinical providers, not limited to therapists, psychologists, nurses, and other healthcare facilities such as nursing homes and hospitals.

BRIEF DESCRIPTION OF THE DRAWINGS

Reference will now be made to the attached drawings, when read in combination with the following detailed description, wherein like reference numerals refer to like parts throughout the several views, and in which:

FIG. 4 is a spreadsheet depiction of a care value index AHA (ACO)/SC spine program;

FIG. 7 is a MODUS (loosely defined as an operational model for sharing risks and rewards between healthcare payers, providers and patients) client spine spreadsheet illustration similar to FIG. 4 and which provides an exemplary breakdown of primary care physicians (PCP's) and associated specialists (spine surgeon, chiropractor, psychologist, physical therapist, etc.) for a given client, such further illustrating such as best practices scores, overall percentage ratings, patient satisfaction, payer cost and shared savings, the payments provided by the ACO for the patient/client being bundled in a designated amount and thereafter distributed to the various providers as per the scorecard ratings achieved;

FIG. 8 is an illustration of a patient enrollment screen display, such as associated with the patient kiosk module, and which provides entry fields for enabling the patient to provide necessary information for the system, the incentive for entering can include specified rewards (e.g. gift certificates, etc.);

FIG. 9 is a screen illustration of an editable preferred specialty providers page associated with the scorecard aspects of the system and computer writeable medium and which provides detail as to particular treatment options and protocols administered by that provider (such as which are condition specific in particular regards to spinal pain treatment) and along with corresponding best practice ratings;

FIG. 10 is a first colored (purple) flag screen illustration generated according to the best practices protocol and associated decision support system, resulting from an initial patient analysis and diagnosis, and with a recommendation for treatment of a diagnosed impaired function of the patient by a primary care physician with specified (desired) options;

FIG. 11 is a succeeding illustration to FIG. 10 and depicting a management generated report based on the initial treatment decisions of the primary care physician;

FIG. 12 a second colored (yellow) flag screen illustration generated according to the best practices protocol and associated decision support system, resulting from an alternate initial or further patient analysis and diagnosis (to that provided in FIG. 10) and indicating an increase in the patient's anxiety level, and with a recommendation for treatment of the patient by a primary care physician with additional specified (desired) options;

FIG. 13 is a succeeding illustration to FIG. 12 and depicting a management generated report based on the decisions of the primary care physician;

FIG. 14 is a third colored (red) flag screen illustration generated according to the best practices protocol and associated decision support system, resulting from a succeeding and updated patient diagnosis to that assessed in FIG. 10, and with a recommendation for a referral by the primary care physician such as to a specialist;

FIG. 17 is a management screen display and which provides compliance ratings for care providers, based upon stages or gradations of care ranging from in clinic care from the primary physician through specialist care and surgery.

DETAILED DESCRIPTION OF THE PREFERRED EMBODIMENTS

Figure 5:
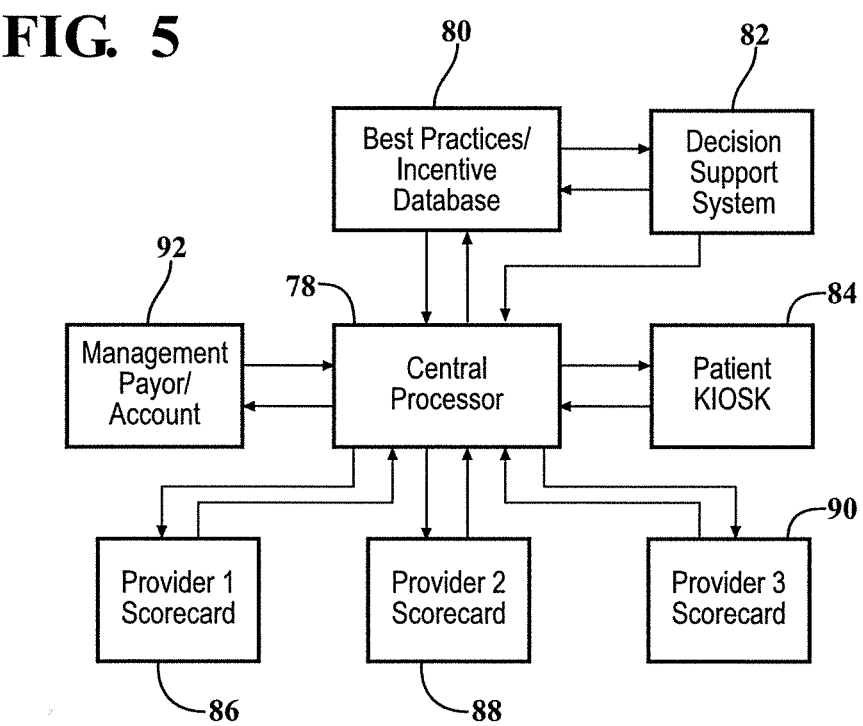
FIG. 5 is a flow diagram of the present system and which illustrates the interactive nature of the central processor which interfaces with each of the best brackets/incentive database, associated decision support system, patient kiosk, provider scorecards and payor/ACO interface.

With reference initially to FIGS. 1-4, a first non-limiting application of the present system, method and software/ algorithmic based computer medium is depicted in the form of a specific spinal pain related application of the present invention, it being understood that, with succeeding reference to FIG. 5 et seq., the present inventions are applicable to any situation dealing with the providing of services, such not limited to any subset arear of specialty involving the delivery of healthcare and can be equally applicable to non-medical related models in which the desire is to retrain/ incentivize the various service providers to focus on adherence to a best practices model and actual/verifiable patient/ client outcomes, and as opposed to basing such incentives and compensation on the quantity of service provided.

Referring again to the particular model of FIGS. 1-4, from a statistical standpoint, approximately 80% of the population will experience some level of spinal pain at some point in their lifetime. At any given time, 31% of the population suffers from an existing spinal related issue. Spinal fusion procedures currently account for the number 1 inpatient cost with spinal pain currently also the number 1 outpatient cost and second highest reason for work absenteeism. Other factors relating to the costs of spinal pain and associated conditions include incidences of emergency room visits (#3 for females and #5 for males for age groups 15-65), the cost to the U.S. economy (presently $100 billion per year) and the percentage (41% to 87%) of worker compensation costs.

Existing spinal treatment protocols, such as in particular first or second level fusion of spinal vertebrae, further often result in significant costs (surgical and hospital including for operating room, anesthesiologist, follow up care, etc.) as well as patient downtime during recovery. An outcome study in the state of Washington found 100% disability rate for patient undergone spinal fusion surgery. Other medical conditions associated with persistent back pain, notably anxiety and depression, are a major factor in worsening the patient outcome and the current care model fails to address the anxiety and depression because the care for these conditions is not as lucrative as doing procedures on these patients. In lieu of this, editable management options are provided for various providers group preferences, along with color and numbers visual real-time feedback to users about their compliance score (with subsequent reference to FIG. 17).

As a result of the fee for service payment system, providers are rewarded for doing more (procedures or medication prescriptions) regardless of the patient medical or functional outcomes. Currently, the medical system has very limited mechanisms to hold providers accountable for their work and providers are often in fact rewarded for doing and providing more care (and not necessarily better care) for their patients.

Existing treatment schemes (including fee for service models) reward care providers in volume as opposed to effectiveness of the care, resulting in significantly diminished returns on investment (as referenced in the apex point depicted in the graph of FIG. 3), with even decreased returns for significant additional investment as reflected in patient morbidity and mortality. Providers compliance with best practice guidelines for spine pain has always been low and in the study by Mafi et al 2013, the compliance with best practices it being noted as worsening over the past decade.

Figure 1:
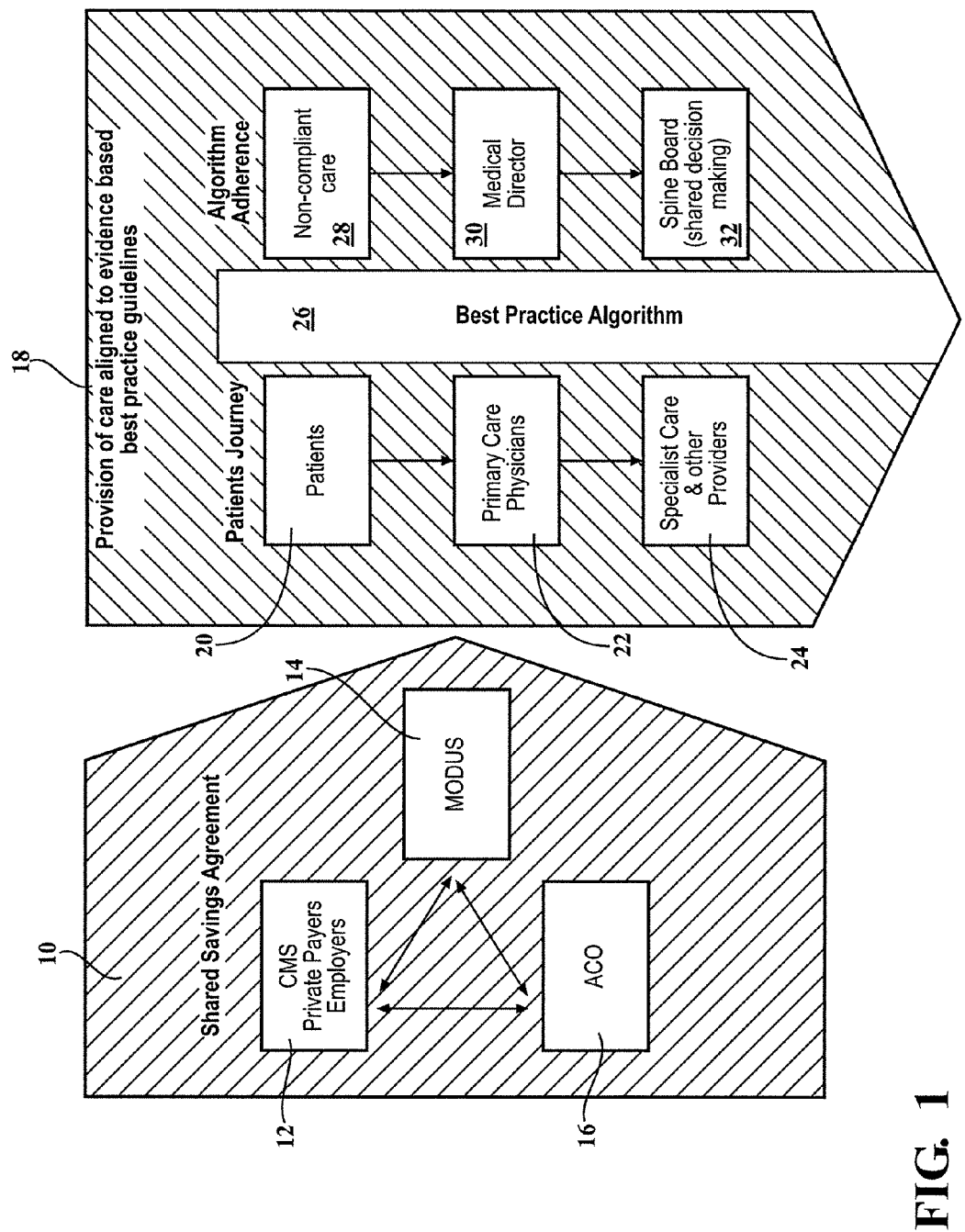
FIG. 1 is a schematic of an operational model according to one non-limiting aspect of the present invention and which combines aspects of shared savings agreements as applied to provisional of level of care aligned to evidence based best practice guidelines.

In response to the above conditions, the present system enables health care payers and to recognize value and pay for the provider's results instead of just paying for efforts. Beyond that, the present invention seeks to combine system, process and algorithmic based medium for establishing a best practices protocol for treating a variety of medical conditions (including spinal pain management). Referring first to FIG. 1, a schematic of an operational model is provided according to one non-limiting aspect of the present invention and which combines aspects of shared savings agreements as applied to provisional of level of care aligned to evidence based best practice guidelines. The present system will measure data on clinical providers in regards to each of best practice compliance, patient's functional outcomes and patient satisfaction. The unique data will further enable the payers to reward providers for their patients outcomes and not just for efforts (e.g. such as again measured in volume of service or care provided). Such a system effectively makes the providers accountable to their patients and payers.

FIG. 1 illustrates, at 10, an overall representation of a shared services agreement and which encompasses the interactive aspects of a CMS (Centers for Medicare/Medicaid Services) Private Payers Employers 12, scientific consultants 14 and ACO (Accountable Care Organizations). By definition, ACO's are groups of doctors, hospitals and other healthcare providers that share responsibility for providing care for their patients. By coordinating their efforts, these groups provide higher-quality care in a more cost-efficient manner. They then share in the profits from the savings that result. As further defined, an Accountable Care Organization can be developed through the Centers for Medicaid and Medicare (CMS) or privately outside of the CMS structure.

The shared services agreement (module) 10 interfaces with a further module 18 encompassing a provisional of level of care aligned to evidence based best practice guidelines. A patient journey component includes designations for patients 20, primary care physicians 22 and specialist care and other providers 24. A best practices algorithm (see as generally represented at 26 in FIG. 1 and further delineated in FIG. 2) is provided and interfaces the patient journey components with algorithm adherence aspects including each of non-compliant care 28, medical director 30 and spine board 32.

Figure 2:
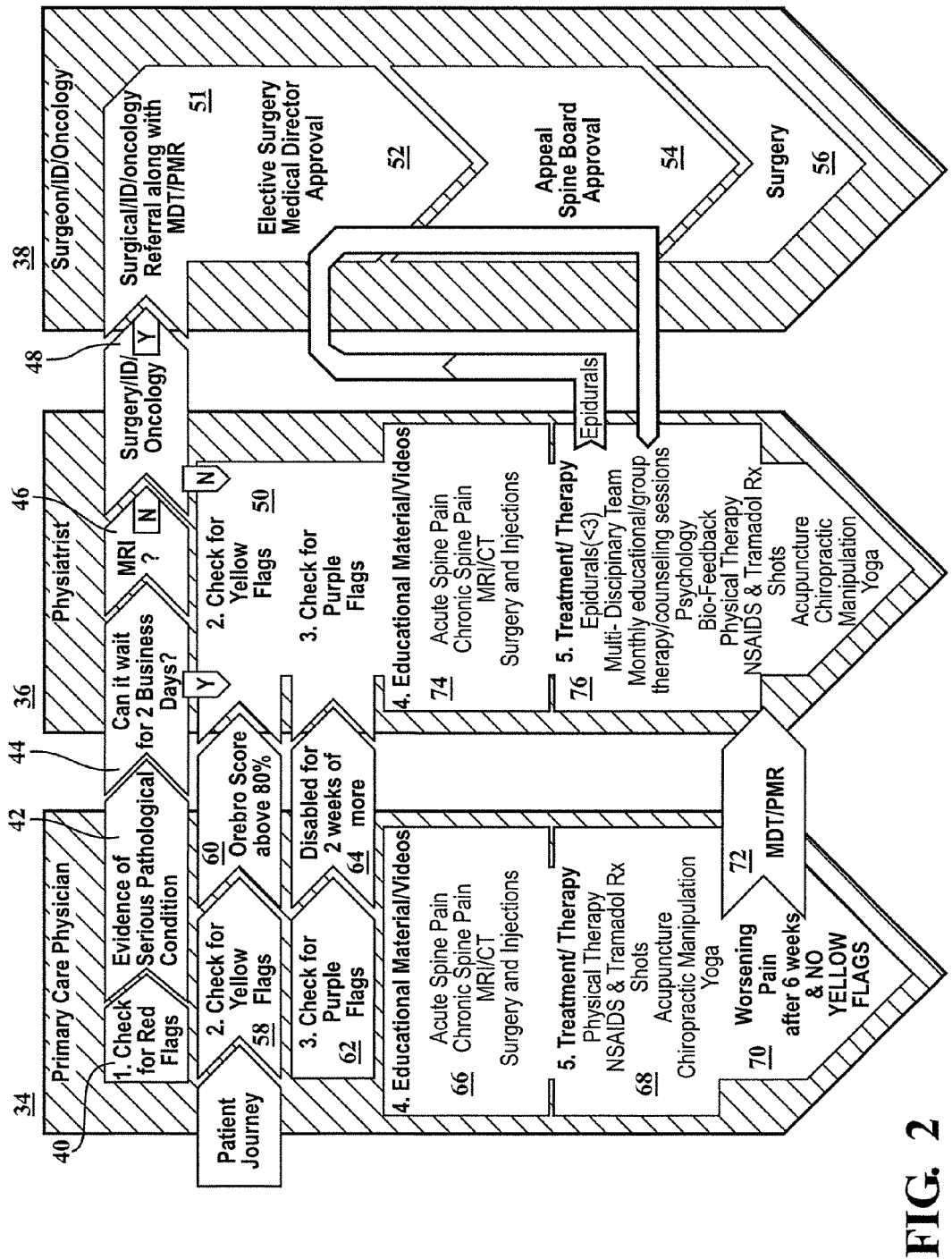
FIG. 2 is a related representation of a best practices algorithm dealing with interactive events involving each of a primary care physician, physiatrist and surgeon.
Figure 3:
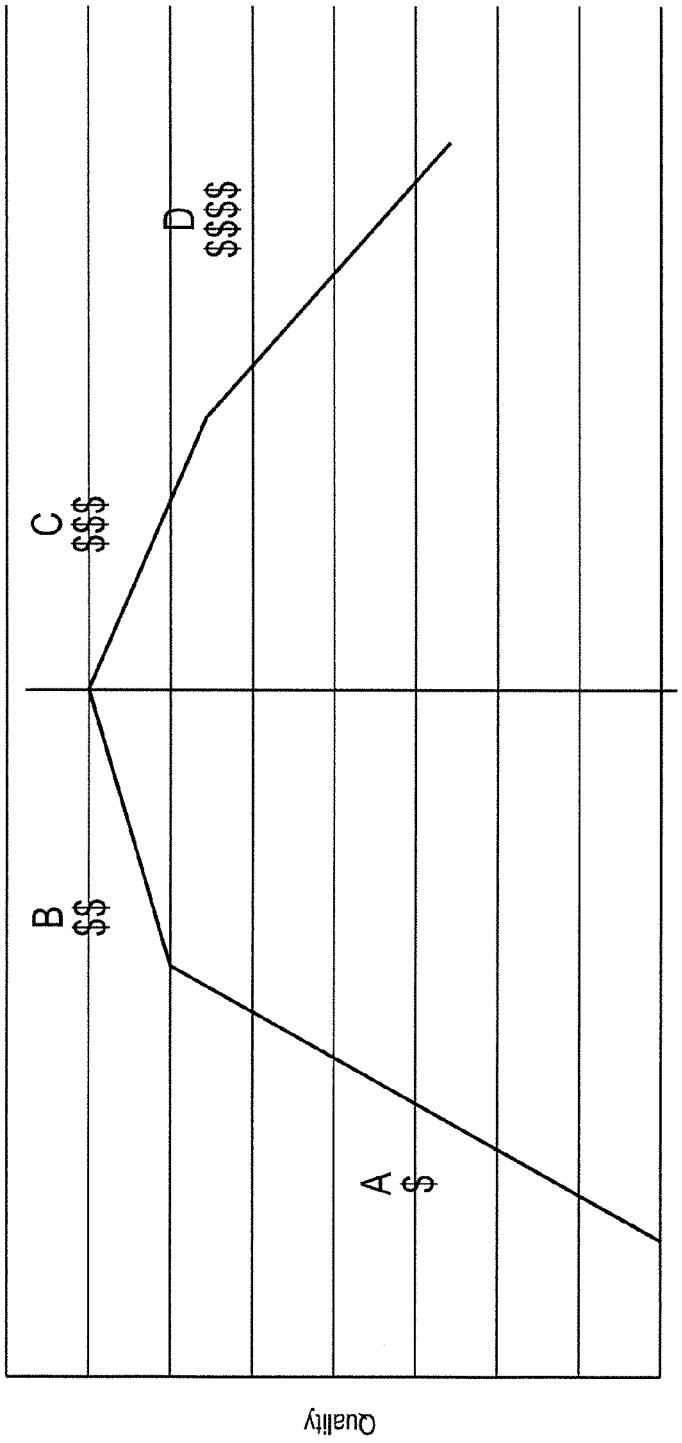
FIG. 3 is a graph depicting Quality versus Spending and which identifies a maximum point of return on investment.

Proceeding to FIG. 2, a related representation of the best practices algorithm 26 is provided and detail dealing with interactive events involving each of a primary care physician 34, physiatrist 36 and surgeon 38 components. The patient journey starts with either the primary care physician, a physiatrist or a spine surgeon and they all initiate the care by checking, at step 1 (40), for any immediate red flags which are evidenced of serious pathological conditions (42) then checking for yellow flags associated with catastrophizing responses by the patient who will need multi-disciplinary care tem (that includes psychological care) and everyone checks for purple flags (documenting the patient functional level) 36.

A magnetic resonance imaging (MRI) 44 step can succeed the evaluation step 42, following which a surgical recommendation 46 of the physiatrist. By definition, a physiatrist/rehabilitation physicians is a medical doctor who has completed training in the medical specialty of physical medicine and rehabilitation (PM&R). Specifically, rehabilitation physicians provide each of diagnosing and treatment of pain, restoration of maximum function lost through injury, illness or disabling conditions, treatment of the whole person, not just the problem area, leading a team of medical professionals, providing non-surgical treatments, and managing medical problems and treatment/prevention plans.

By further definition, the job of a rehabilitation physician is to treat any disability resulting from disease or injury, from sore shoulders to spinal cord injuries. The focus is on the development of a comprehensive program for putting the pieces of a person's life back together after injury or disease—without surgery unnecessary medical procedures and by incorporating the shared decision protocols integrated into the present inventions.

Rehabilitation physicians are doctors of function, they take the time needed to accurately pinpoint the source of an ailment. They then design a treatment plan that can be carried out by the patients themselves or with the help of the rehabilitation physician's medical team. This medical team might include other physicians and health professionals. These include such as psychologists, physical therapists, occupational therapists, health coaches, athletic trainers, social workers, neurologists, orthopedic surgeons, and physical therapists. By providing an appropriate treatment plan, rehabilitation physicians help patients stay as active as possible at any age. Their broad medical expertise allows them to treat disabling conditions throughout a person's lifetime.

Surgical recommendation 46 can result in yes 48 or no 50 steps. If yes, surgeon 38 module is activated and results in a surgical referral 51, progressing to an elective surgery medical director approval step 52, appeal of a spine board approval 54 and, finally, surgery 56.

Alternate to red flag step 40, a check for yellow flag step 58 proceeds to a determination if an Örebro score exceeds 80% (at step 60). The same occurs at previously identified step 50 in the instance of the physiatrist (module 36) determining that surgery is not an option.

The Örebro Musculoskeletal Pain Questionnaire (ÖMPQ), formerly known as the Acute Low Back Pain Screening Questionnaire (ALBPSQ), was developed to help identify patients at risk for developing persistent back pain problems and related disability.

The questionnaire is intended to be used with individuals who are experiencing regional pain problems that are affecting their performance at work, taking repeated short spells of sickness absence or are currently off work. In one version of the questionnaire, there are twenty one scored questions concerning attitudes and beliefs, behaviour in response to pain, affect, perception of work and activities of daily living.

The questionnaire can usually be completed in 5 min before the patient meets the health professional. A cut-off score of 105 and below has been found to predict, with 95% accuracy, those who will recover and, with 81% accuracy, those who will have no further sick leave, in the next 6 months.

Prediction of long-term sick leave (>30 days within the next 6 months) was found to be 67% accurate. A cut-off score of 130 and above correctly predicted 86% of those who failed to return to work. The effect of this score is to assist the clinician to apply interventions (including the use of activity programs based on cognitive behavioural strategies) to reduce the risk of long-term pain-related disability. Evidence indicates that these factors can be changed if they are addressed. It has also been found that the total score is a relatively good predictor of future absenteeism due to sickness absence as well as function, but not of pain. The results suggest that the instrument could be of value in isolating patients in need of early interventions and may promote the use of appropriate interventions for patients with psychological risk factors.

The primary care physician module 34 includes a further step 62 for checking for the existence of a purple flag, this further indicating at step 64 that the patient is likely disabled for two weeks or more (in turn leading to a similar purple flag analysis within physiatrist module 36). Additional steps associated with the primary care physician module 34 include each of step 66 for providing (to the patient)

education material/videos relating to acute/chronic spinal pain, MRI or CT (computed tomography) procedures, surgery and associated injections, as well as step 68 for providing treatment/therapy options (physical therapy, non-steroidal anti-inflammatory drugs or NSAIDS, Tramadol Rx shots, Acupuncture, chiropractic manipulation and yoga). Following these steps, and if worsening pain persists after six weeks with no yellow flags (step 70), an MRI procedure is performed at step 72 when advancing to the physiatrist module 36.

Physiatrist module also includes a similar step 74 (as compared to at 66 in physician module 34). Step 76 recites additional treatment/therapy protocols including up to three epidural procedures (see further feedback loop interfacing with surgical module 38 and steps 52-54. Additional aspects of step 76 include each of use of multi-disciplinary teams, psychology, bio-feedback and other aspects previously recited in step 68.

Additional aspects of the invention include the provision of a suitable software component for effectuating some or all of the objects of the invention, such including interfacing each of the modules 34, 36 and 38 of the best practice algorithm, this in order to most effectively and efficiently providing for communication between the various care providers and in order to enforce the objectives of the best practices protocol in order to avoid excessive treatments/procedures and, most notably, unnecessary surgeries in order to effectively treat many types of spinal ailments. The software module is understood to interface with any suitable processor driven tablet, hand-held smart phone, laptop, PC or the like in order to quickly and efficiently interface each of the medical providers or other specialists described herein.

The care value index of FIG. 4, see at 75, provides one non-limiting example of a tabular arrangement for providing a breakdown of individual metrics for any plurality of care providers not limited to primary care physicians (PCP's) and specialty care physicians such as spinal surgeons, chiropractors, psychologists and the like. Referencing the table of FIG. 4, the purpose for this is to provide one non-limiting example of a series of metrics which can be used in establishing a supporting financial model for assisting in incorporating an existing/most recently updated best practices protocol and in order to determine both the maximum efficiency of investment referenced in FIG. 3 (graph 75 depicting Quality versus Spending and which identifies a maximum point of return on investment), along with providing a readily accessible model for properly acknowledging and rewarding a provider for both adhering to the best practices protocol. In concert with the above description, the objects of the present invention include the ability to partner with providers networks in order to achieve better patient clinical and functional outcomes at lower cost. By rewarding providers for integration, care coordination, adopting evidence based best practice and peer review, the present system results in minimizing unnecessary care which will result in benefits for patients, practitioners, employers, employees and third parties.

Proceeding to FIG. 5, a flow diagram is provided of the present system and which illustrates the interactive nature of a central processor 78, which interfaces with each of a best brackets/incentive database 80, an associated decision support system module 82, a patient kiosk 84, and a plurality of subset devices 86, 88, 90, et seq., associated with each of a designated group of individuals or entities associate with a service provider organization (such ranging from an individual physician to a practice group including classes of primary care physicians, specialists/surgeons, physical care specialists and the like). Also depicted at 92 is payor/ACO module which likewise interfaces with the central processor 78 and can include a separate computer, laptop or any other processor driven device. The payor/ACO module is also generally designated as a management model and to account for the fact that the payor/ACO may elect to designate an outside supervisory entity.

Without limitation, the processor 78 can include any type of computing device not limited to a hard drive containing computer, laptop, etc., as well as a cloud based processor or database. The subset devices 86, 88, 90 et seq. can further be provided as any of a laptop, tablet computer, smart phone or the like and which are in wired or wireless, including 3G, 4G LTE, Bluetooth, or NFC (near field communication) with the central processor and its output functions.

As will also be now described with reference to FIG. 6 et seq., the implementation and performance of the present system and method relies upon the creation of an effective algorithmic based software program which is loaded into or otherwise interfaced with the central processor 78 and its various communicating components 80-92. Such a software program can include various modules or components associated with each of the hardware devices, in one instance a first software module associated with the central processor module 78, as well as its interfacing lookup table incorporating the best practices model and the attendant decision support system, and which also includes additional subset modules in interfacing/two-way communication with the central processor and module, such subset modules also envisioning being in the form of a mobile application which can be accessed by any of a laptop, tablet or smart phone.

Figure 6:
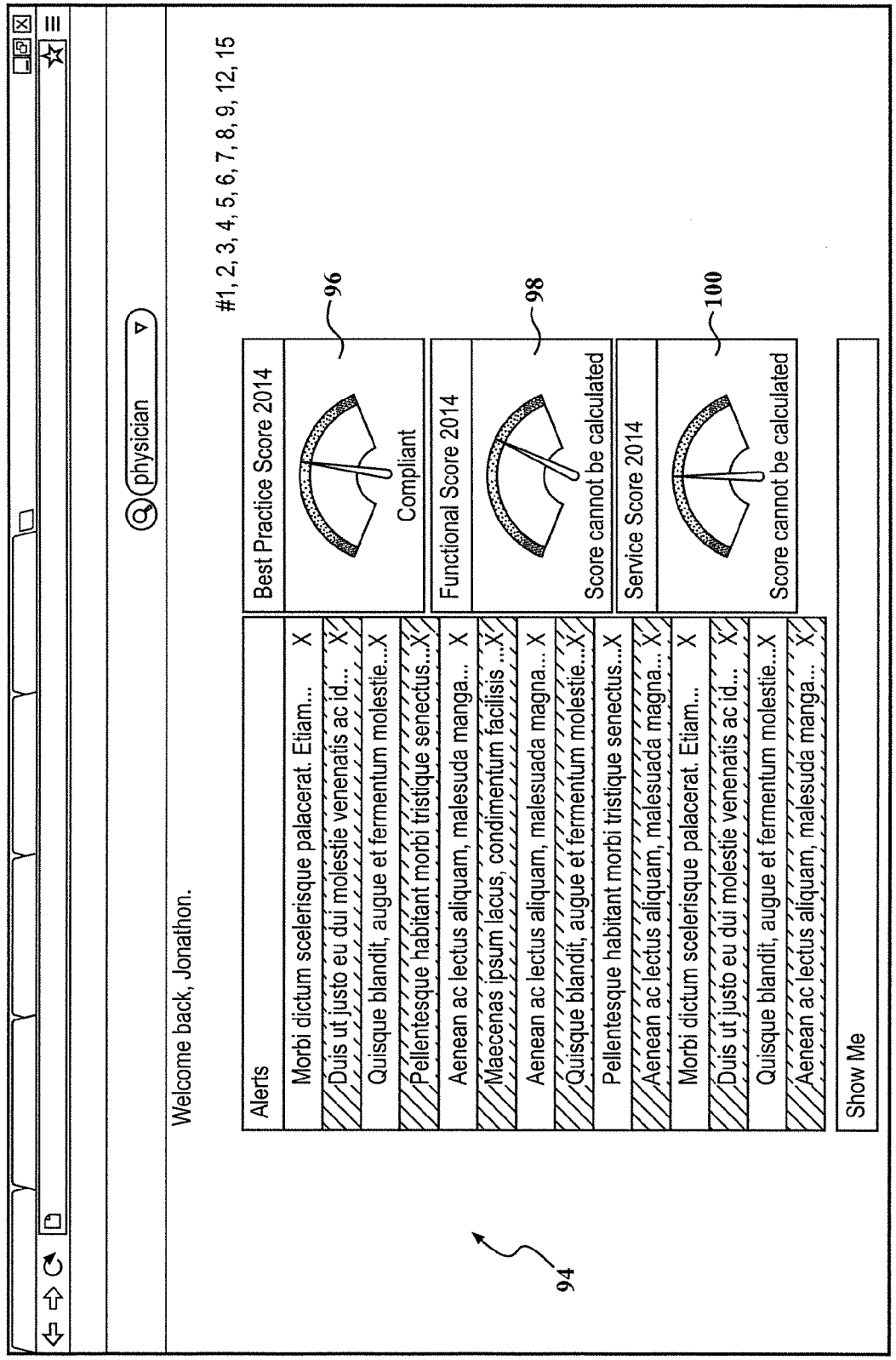
FIG. 6 is a first screen shot illustration of a best practices driven scorecard which is derived from the present system and non-transitory computer writeable medium for providing a rating of the physician or other care provider on the basis of adherence to the practice objectives and protocols established by the ACO or other designated authority.

Referring to FIG. 6 is a first screen shot illustration is provided at 94 of a best practices driven scorecard which is derived from the present system and non-transitory computer writeable medium for providing a rating of the physician or other care provider on the basis of adherence to the practice objectives and protocols established by the ACO or other designated authority. Without limitation, this can include providing an ongoing rating (such as on a yearly basis) on a percentage basis of an achieved best practices score (see for example at 57% at 96), as well functional score (further example shown at 68% at 98) and service score 100.

FIG. 7 is a spreadsheet illustration, at 102 and similar to as shown at 75 in FIG. 4, and which provides an exemplary breakdown of primary care physicians (PCP's on line item 6) and associated specialists (spine surgeon on line 36, chiropractor on line 38, psychologist on line 40, physical therapist on line 42, etc.) for a given client, in this instance associated with a spinal treatment program. This illustration further itemizes such as best practices scores, overall percentage ratings, patient satisfaction, payer cost and shared savings, the payments provided by the ACO for the patient/client being bundled in a designated amount and thereafter distributed to the various providers as per the scorecard ratings achieved. The spreadsheet illustrations of FIGS. 4 and 7 can generally represent one output and illustrative function associated with the management (ACO/payer) module 92 and which assists in tracking the breakdown and distribution of lump sum budgets which are allocated to a given practice group/service provider.

FIG. 8 is an illustration, at 104, of a patient enrollment screen display, such as associated with the patient kiosk module, and which provides a series of biographical or other entry fields for enabling the patient to provide necessary information for the system. The present inventions contemplate the participation of the patient/client, not only in the inputting of information which is more efficiently obtained directly as opposed to being recorded by other personnel, but also in the ability to provide the patient/client with the ability to comment on the performance of the care provider to further assist in assessing and scoring the performance metrics of that provider. The present inventions contemplate providing incentives to the patient for his/her participation and such can include specified rewards (e.g. gift certificates, discounts, etc.) for providing the requested information.

Figure 9:
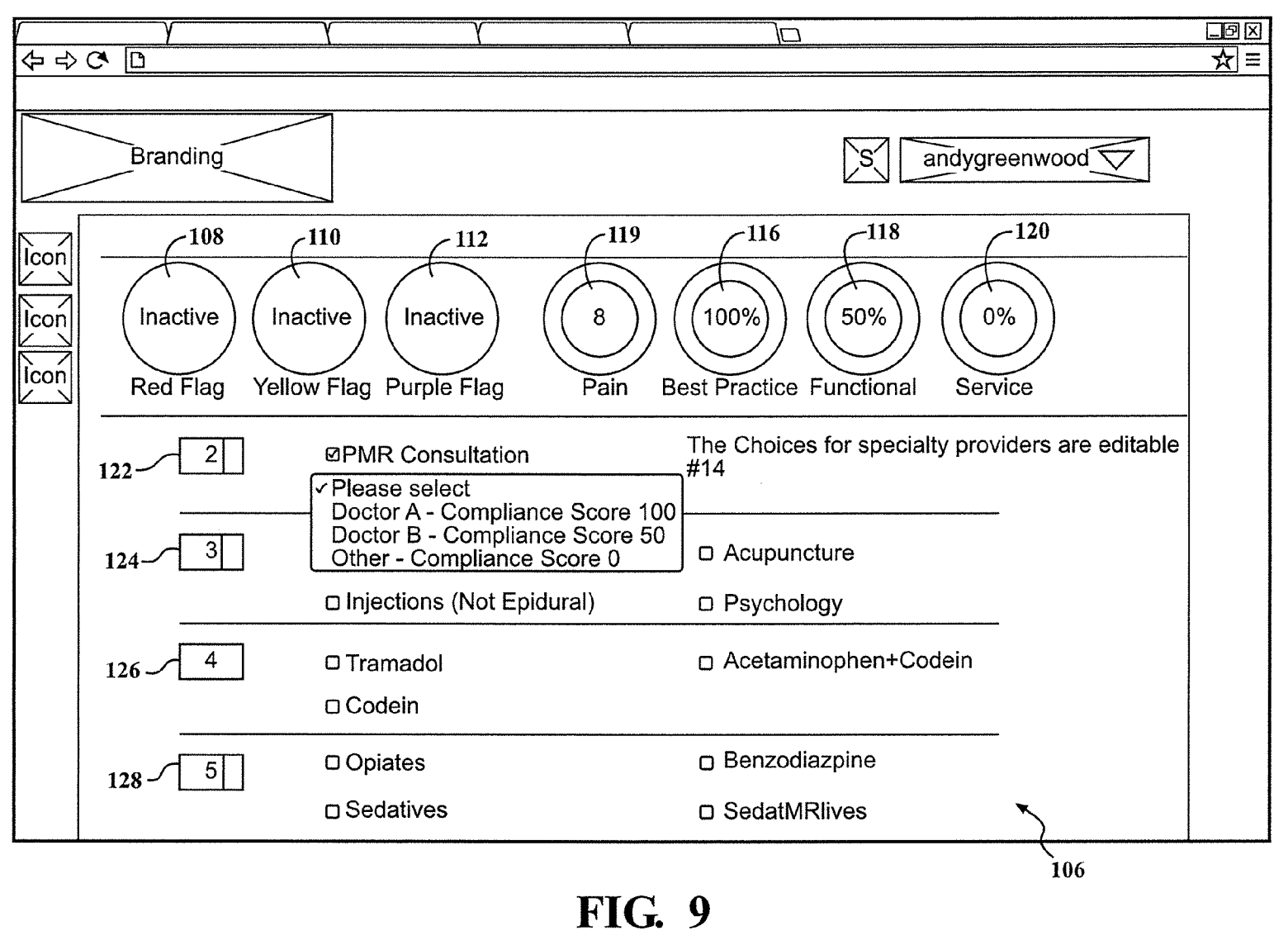

FIG. 9 is a screen illustration of an editable preferred specialty providers page, see generally at 106, associated with the scorecard aspects of the system and computer writeable medium and which provides detail as to particular treatment options and protocols administered by that provider (such as which are condition specific in particular regards to spinal pain treatment) and along with corresponding best practice ratings). As will be described with additional detail in reference to succeeding FIGS. 10-17, the specialty provider's page can designate any one of a red 108, yellow 110 or purple 112 flag, as well as providing a pain level indicator 114, a best practice compliance score field 116, a functional field 118 and a service field 120. Additional designations 122-128 in FIG. 9 can reference color coding for each of a succession of treatment option subsets, respectively at 2-5, and associated with various stages of spinal pain treatment.

Figure 11:
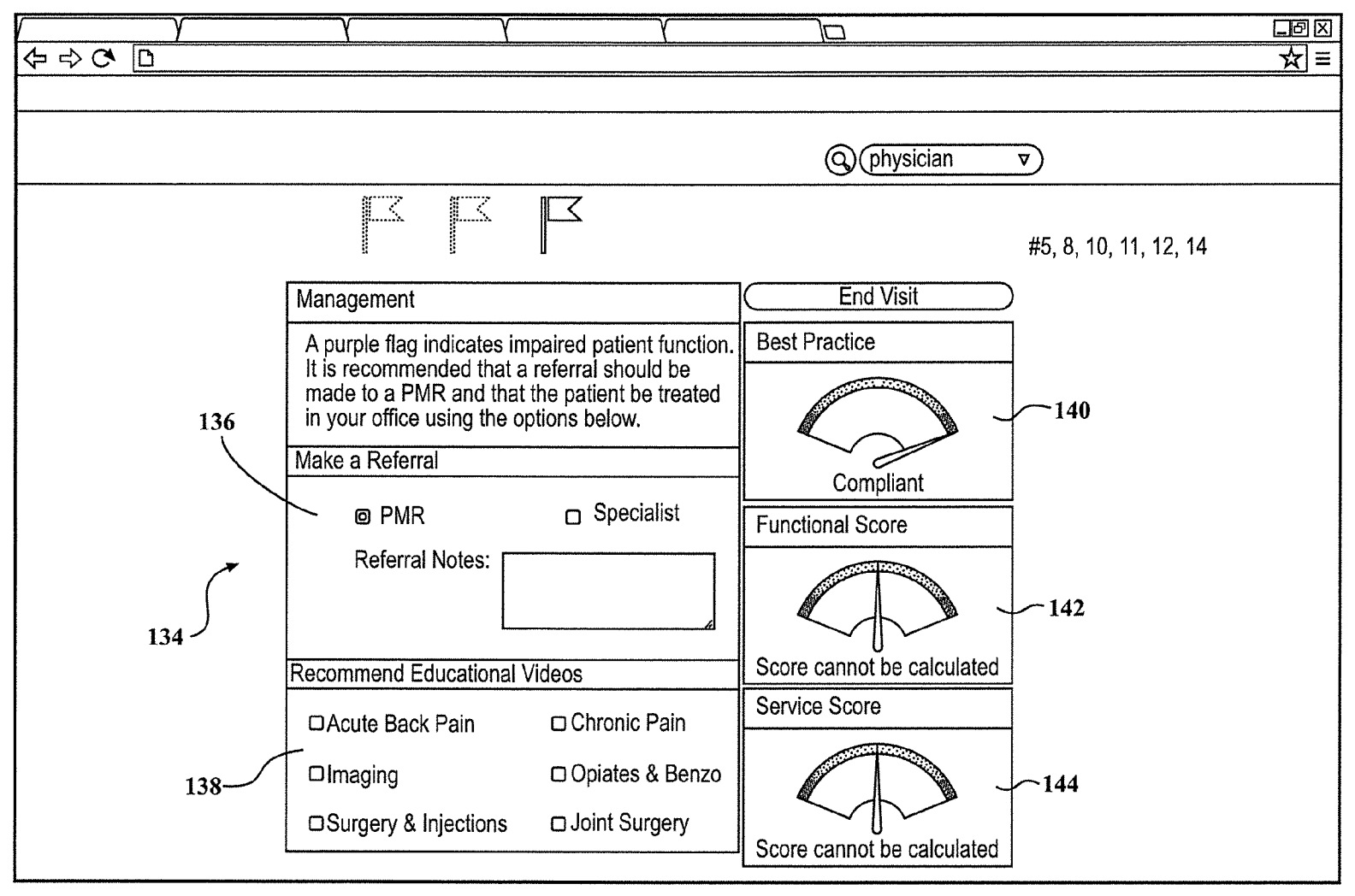

FIG. 10 is a first colored (purple) flag screen illustration 139, such as which can be associated with the management module 92, and which is generated according to the best practices protocol and associated decision support system, and resulting from an initial patient analysis and diagnosis, and with a recommendation for treatment of a diagnosed impaired function of the patient by a primary care physician with specified (desired) options. Also depicted at 132 is a field designating that care provider's functional score in terms of best practice compliance. FIG. 11 is a succeeding illustration to FIG. 10 and depicting a management generated report 134 based on the initial treatment decisions of the primary care physician and including entry fields for referrals 136, recommended educational videos 138, as well as rating identifiers (such as provided on a percentage basis) and again including best practice 140, functional score 142 and service score 144.

Figure 13:
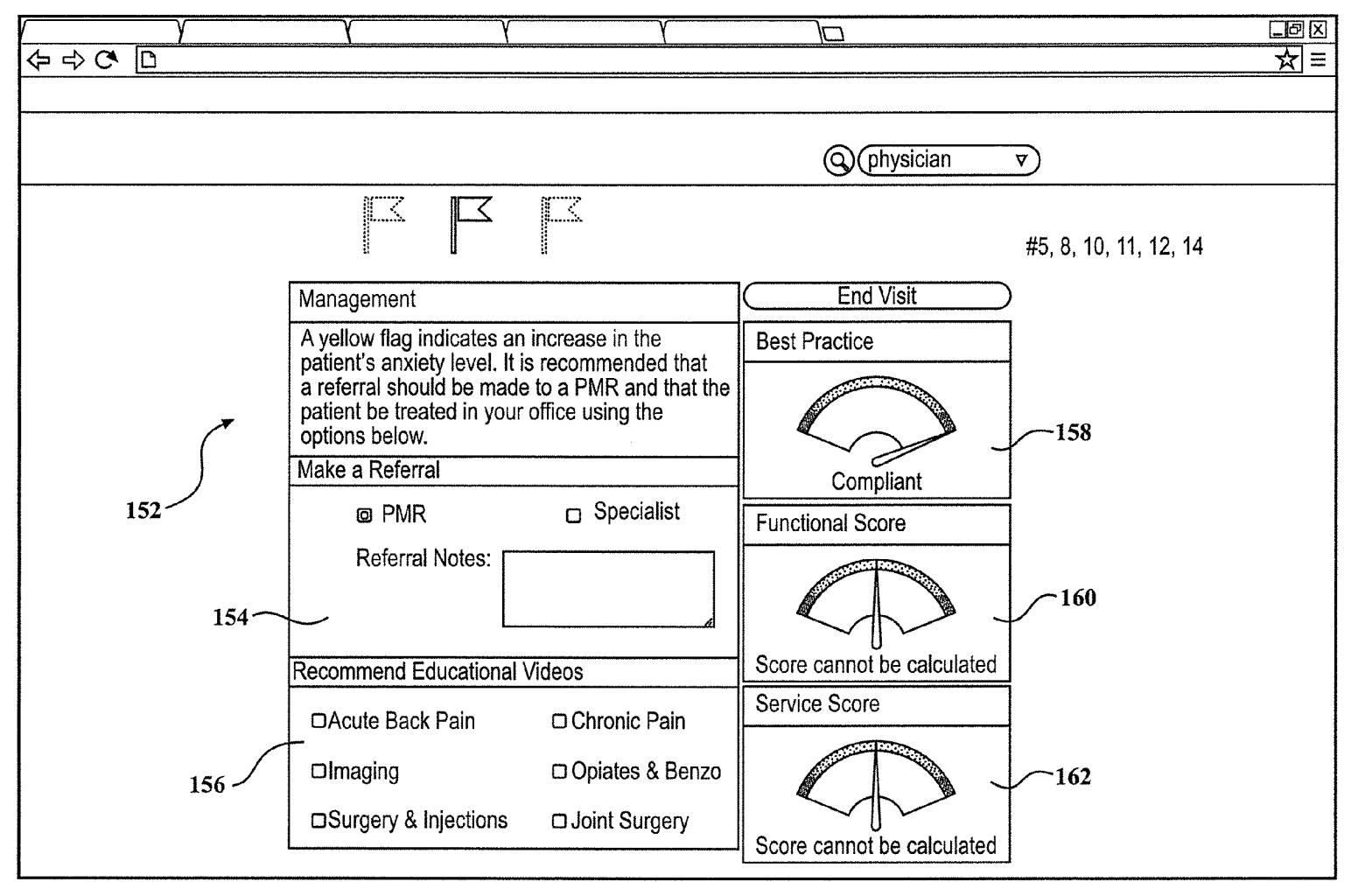

FIG. 12 a second colored (yellow) flag screen illustration 146 generated according to the best practices protocol and associated decision support system, this resulting from an alternate initial or further patient analysis and diagnosis (to that provided in FIG. 10) and indicating an increase in the patient's anxiety level (at field 148), and with a recommendation for treatment of the patient by a primary care physician (150) with additional specified (desired) options. FIG. 13 is a succeeding illustration to FIG. 12 and depicting a management generated report 152 based on the decisions of the primary care physician, along with and including entry fields for referrals 154, recommended educational videos 156, as well as rating identifiers (such as provided on a percentage basis) and again including best practice 158, functional score 160 and service score 162. In application, this designation can further provide a final service outcome (the scorecard) that MODUS (as defined herein) provides.

Figure 15:
FIG. 15 is a succeeding illustration to FIG. 12 and depicting a management generated report based on the decisions of the specialist.

FIG. 14 is a third colored (red) flag screen illustration 164 generated according to the best practices protocol and associated decision support system, resulting from a succeeding and updated patient diagnosis to that assessed in FIG. 10, and with a recommendation, at 166, for a referral by the primary care physician such as to a specialist. FIG. 15 is a succeeding illustration to FIG. 12 and depicting a management generated report 168 based on the decisions of the specialist, such including a diagnosis field 170, referral field 172 and repeat of compliance ratings for best practice (not compliant as designated at 174), functional score 176 and service score 178.

Figure 16:
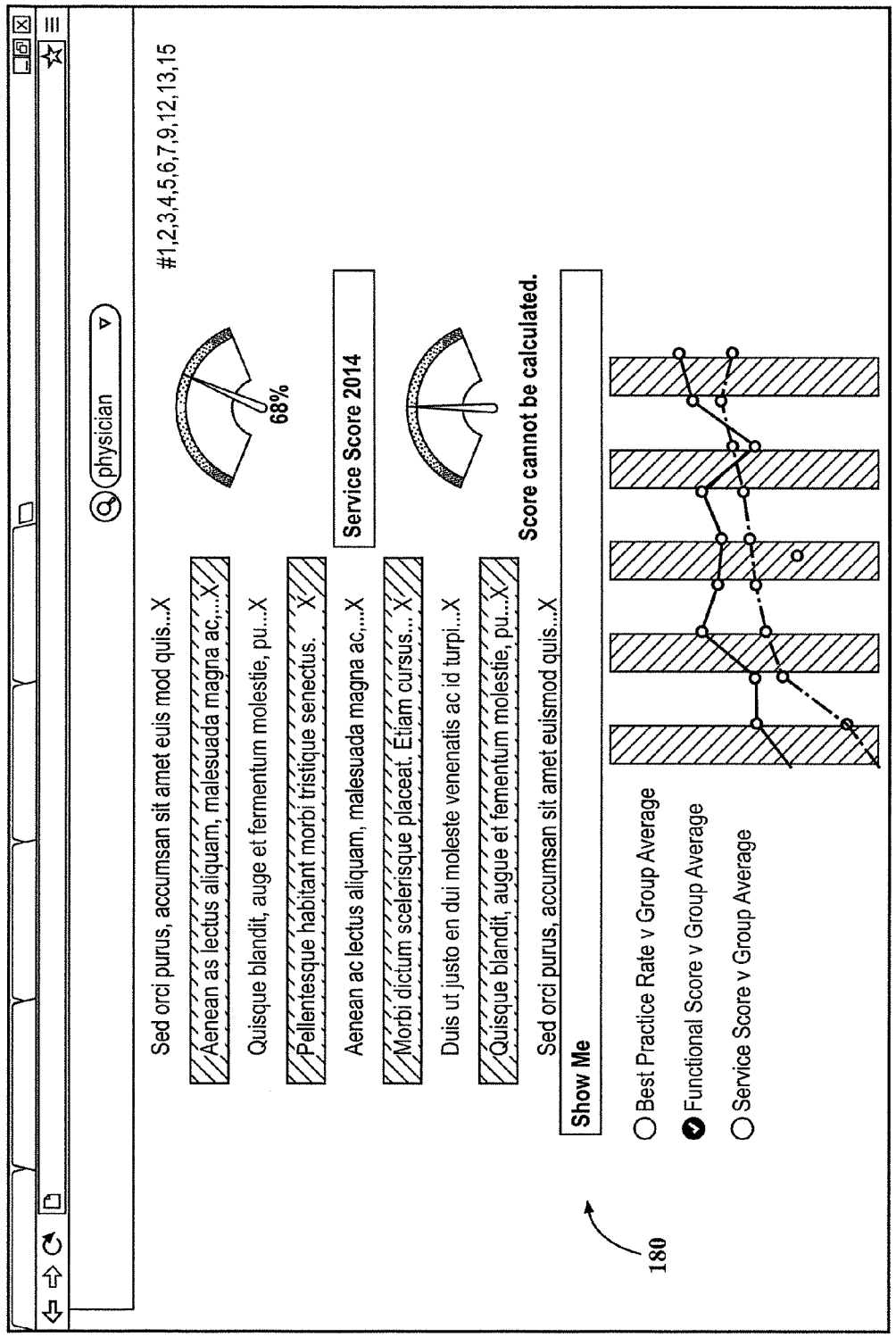
FIG. 16 is a screen display of a comparison graph of a functional score vs. group average for a given physician.
Figure 17:
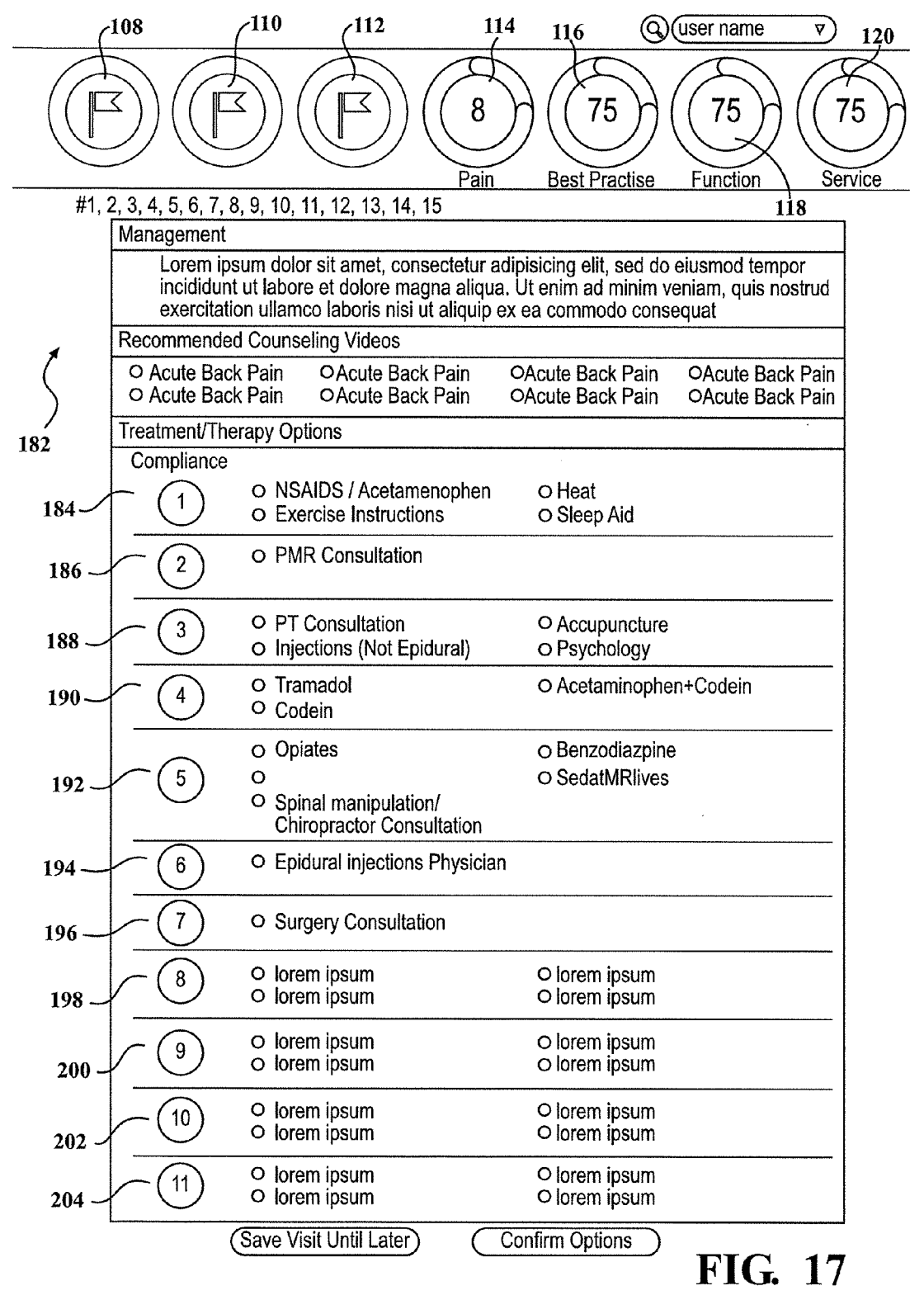

FIG. 16 is a screen display 180 of a comparison graph of a functional score vs. group average for a given physician and which assists in tracking the real time performance of that individual relative to the overall group. Finally, FIG. 17 is a management screen display and which provides compliance ratings for care providers, based upon stages or gradations of care ranging from in clinic care from the primary physician through specialist care and surgery. The flag and rating fields 108-120 described in FIG. 9 are repeated, along with additional fields 184-204, these respectively designating a scale of compliance ranging from 1 (least intensive) to 11 (most intensive).

In application, the software/algorithmic based protocol can function in one instance to create a series of subroutines for operating the present system and which include a first such subroutine for assembling a best practices model in the form of a database interfacing with the processor device and which presents series of treatment options ranging from desirable to undesirable associated with a given type of service. A second subroutine provides a decision support system interfacing with the best practices database and processor device, the support system providing any of a grading or awarding system for scoring, in real time, performance metrics for each of any number of providers of the service.

A third subroutine outputs to a plurality of subset processor devices assigned to each of the providers, real time and continuously updated scoring of their performance metrics based upon the grading/awarding system and as a result of the treatment options selected and inputted by the provider. A fourth subroutine (such as which can be integrated into the third subroutine) incentivizes adherence by the providers to the best practices model by tying desirable performance metrics to financial incentives which are scaled to each treatment option.

Additional subroutines include providing and incentivizing patient input to the processor driven device in the form of at least one of medical/biographical data input and commentary/rating regarding the service provider. A management module can also include at least one additional subroutine interfacing with the processor driven device for monitoring and tracking adherence to the best practices model.

Additional subroutines can designate a sum of funds representative of an operating budget for the service provider and for disbursement on a percentage basis to each of any number of subset service providers based upon adherence to the best practices model. This can further include subdividing the sum between different practice groups and sub-specialties associated with a given class of service providers.

Addressing the initial example described in FIGS. 1-4, one subset application of the software based algorithmic medium can in particular include the treatment options associated with said first subroutine further including being integrated into a medical care protocol and further including any one or more of a first physician service provider assessing a patient's condition, a second physiatrist service provider further assessing the patient and interfacing with said first physician in an extreme diagnostic event, and a third surgeon service provider for additionally assessing the patient and interfacing with the second physiatrist service provider in at least an epidural related event. This can further include an MRI procedure associated with an interfacing event between the physician and physiatrist modules.

Given the above description, the present invention (including each and all of the system, method and non-transitory computer writeable medium) accordingly provides an incentive structure for rewarding care providers based upon best practice decision making (quality or outcome dependent) and not merely upon quantity of services provided (e.g. tests ordered, surgical procedures conducted etc.). In this manner, health care dollars are more equitably distributed as well as saved by such a merit/outcome based sharing and distribution scheme, such that the service care provider (physician or other like) can also be paid a bonus as an incentive for keeping their patients/clients more healthy, more able (less disabled) ad more satisfied, as well as preventing the administration of unnecessary treatments and procedures such as are attendant with current quantity of service based compensation models.

Variants of the present system also contemplate a pool or bundle of funds being designated (such representative of historical costs incurred for any given number of physicians or practice groups, including tiers of care providers drawn from PMP (primary care physicians), specialists (cardiology, spinal surgery, etc.), these being paid out on a percentage basis to the various care providers based upon their individual scorecard results regarding adherence to the best practice protocols established by the relevant ACO/care provider, such further reflecting the results/outcome of the treatment provided (i.e., outcome driven performance by the physician or other care provider based results and not compensated as a variable of the quantity of, often unnecessary, services).

Additional advantages include the establishing of performance metrics for clinical providers that are based on adherence to best practice, patient's functional outcome, patient satisfaction and cost. Adherence to the model created in the present invention further derives from the authority implicit in the local ACO or other payer and, along with the creation of transparent metrics for achieving higher compensation levels, serves to more equitably distribute shared savings and other financial incentives between all of the various stake holders (patients, care providers, and payers).

Other advantages of the system include the ability to readily monitor and record the providers/physician's choices in a real-time decision tree which interfaces with the decision support system module and which is reflected in the continually updated scorecard for each such physician/provider. In this fashion, real time feedback to the physician is achieved to monitor ongoing activity in regards to the diagnosis and treatment provided, with the incentive driven compensation structure in place for guiding and influencing such decision making in the directions dictated by the ACO/payer.

In this fashion, the present system, method and computer writeable medium provides a tools to the management portion of the operation or model (e.g. payers, provider organizations, ACO's, etc.) for carrying out the management of the provider's preferences and behavior (as again dictated by the formulated best practices protocols), such further enabling the management portion to control utilization and expenditure of the resources allocated to such care.

In this fashion, customization of the present system is made possible of the best practices formulated, such by the responsible payer or ACO for various types of disease management based upon the manager's (payer's/provider organizations/ACO) preference) and which can further be modified for any criteria or input not limited to differences in geography (i.e. best practices may vary from locale to locale and the present system builds in the flexibility to take this into account). The real-time performance metrics achieved by the present system also enable instant feedback to the providers to both assess current practice and to provide direction (along with accompanying incentives) for adhering to the formulated best practice protocols for present and future treatment of the patient.

The report card aspects also provide comparison metrics for each of the providers/physicians, this further providing a competitive environment (not driven exclusively by dollars) for adopting and adhering to the best practice protocols formulated by the management portion (e.g. including or representing the interests of the payer). The reward mechanism of the present invention is also modified and calibrated to cover any type of care provider (or groups of care providers) not limited to primary care physicians, specialists, or combination/groups of such providers which may be incorporated into a given practice or other entity.

The additional advantage of providing a reward mechanism for participation of the patient (not limited to providing coupons or rebates for undertaking data entry functions), further assists in maximizing the efficiency and economy of the medical records component of the system, as well as assisting in the formulation of correct and unbiased scorecard evaluations of each provider/physician by integrating the patient experience and input into the incentives driving the system.

Summarizing, a listing of the objective made possible by the present inventions include each of the following:

1. Establishing a medical providers scorecard.
2. Providing an operational tool to promote providers collaborations, coordination, integration and shared decision making.
3. Establishing an operational method for bundle payment management.
4. Creating an operational model for paying for performance.
5. Using a reward/incentive system to encourage providers to follow of best practice.
6. Establishing performance metrics for clinical providers that are based on adherence to best practice, patient's functional outcome, patient's satisfaction and cost.
7. Creating a transparent operational model for the distribution of shared savings and other financial incentives between all stakeholders (patients, providers and payers.
8. Monitoring and recording of providers choices in a decision tree.
9. Provide real time, instant feedback for providers compliance with best practice on every patient enrolled in the program.
10. Providing a tool to managers (payers, providers organizations/ACOs) for management of providers preference and behavior and enables the management of providers groups to control utilization.
11. Customizable best practice options for disease management based on the managers (the payers/providers organizations/ACO) preference (given best practice can vary geographically).
12. Providing real time, instant feedback for providers for overall year to date compliance for their patient population.

13. Providing a comparison metric for providers to measure their performance vs others in the group and other groups.
14. Enabling the managers (the payers/providers organizations/ACO) to create and manage an editable specialty physicians providers network.
15. Empowering patients and providers teams by linking the individual provider financial incentives to the patient's and team's experience.
16. Creating a reward mechanism for patients' compliance with care and electronic data entry into the providers medical records system.

Having described my invention, other and additional preferred embodiments will become apparent to those skilled in the art to which it pertains, and without deviating from the scope of the appended claims. In particular, this can include applying the system, method and associated algorithmic based (software) medium to other medical and, potentially, non-medical applications beyond those described herein, such as including but not limited to orthopedics conditions, diabetes care, cardio-pulmonary related chronic conditions, cancer and the like.

Depending further on the chronic condition we are managing, the present system and model will be adjusted accordingly and appropriate clinical providers will be deployed for it and outcome measures will be adjusted to be relevant to the chronic condition. Subject to modification, the providers will generally be PCPs (primary care physicians), then a non-interventional specialist and an interventional specialist. For example in cardiac care the team will include PCPs, cardiologists and interventional cardiologist and cardiac surgeons (along with teams of dietitians, physical therapist, exercise physiologists, trainers) as well as relevant educational material that will be provided to the patients.

I claim:

1. A non-transitory computer readable medium for incentivizing service providers comprising instructions that, upon execution by a hardware processor, cause the hardware processor to:
   execute a first subroutine for assembling a best practices model in the form of a best practices database interfacing with the hardware processor and which presents series of treatment options ranging from desirable to undesirable associated with a given type of service;
   execute a second subroutine providing a decision support system interfacing with the best practices database and hardware processor, the support system providing any of a grading or awarding system for scoring, in real time, performance metrics for each of any number of providers of the service;
   execute a third subroutine for outputting to a plurality of devices assigned to each of the providers, real time and continuously updated scoring of their performance metrics based upon the grading or awarding system and as a result of the treatment options selected and inputted by the providers;
   execute a fourth subroutine for incentivizing adherence by the providers to the best practices model by tying desirable performance metrics to financial incentives which are scaled to each treatment option;
   execute a fifth subroutine for designating a sum of funds representative of an operating budget for a service provider and for disbursement on a percentage basis to each of any number of subset service providers based upon adherence to the best practices model; and
   execute a sixth subroutine for subdividing said sum between different practice groups and sub-specialties associated with a given class of service providers.

2. The non-transitory computer readable medium of claim 1, further comprising an additional subroutine for providing and incentivizing patient input to the hardware processor as medical data input, biographical data input, commentary regarding a service provider, or a rating regarding a service provider.

3. The non-transitory computer readable medium of claim 1, further comprising a management module having at least one additional subroutine interfacing with the hardware processor for monitoring and tracking adherence to the best practices model.

4. The non-transitory computer readable medium of claim 1, wherein said treatment options associated with said first subroutine further comprises being integrated into a medical care protocol and further including any one or more of a first physician service provider assessing a patient's condition, a second physiatrist service provider further assessing the patient and interfacing with said first physician in an extreme diagnostic event, and a third surgeon service provider for additionally assessing the patient and interfacing with the second physiatrist service provider in at least an epidural related event.

5. The non-transitory computer readable medium of claim 1, further comprising an MRI procedure associated with an interfacing event between said physician and physiatrist modules.

6. A system for incentivizing service providers to participate in a best practices and outcome determinant model for providing healthcare, comprising:
   a processor device incorporating a best practices model in the form of a best practices database interfacing with the processor device and which presents series of treatment options ranging from desirable to undesirable associated with each of a number of relevant healthcare services;
   a decision support system interfacing with the best practices database and processor device, the support system providing any of a grading or awarding system for scoring, in real time, performance metrics for each of any number of providers of the service;
   a plurality of subset processor devices assigned to each of the service providers, each of the subset devices recording each selected treatment option provided to a patient, said subset devices interfacing with said processor device and receiving, in real time, continuously updated scoring of their performance metrics based upon the grading or awarding system, including tying desirable performance metrics to financial incentives which are scaled to each treatment option; and
   the decision support system designating a sum of funds representative of an operating budget for a service provider and for disbursement on a percentage basis to each of any number of subset service providers based upon adherence to the best practices model and subdividing said sum between different practice groups and sub-specialties associated with a given class of service providers.

7. The system of claim 6, further comprising a patient kiosk interfacing with the processor device and for inputting to the processor driven device as medical data input, biographical data input, commentary regarding a service provider, or a rating regarding a service provider.

8. The system of claim 6, further comprising a management module having at least one additional subroutine interfacing with the processor driven device for monitoring and tracking adherence to the best practices model.

9. A method for incentivizing service providers to participate in a best practices and outcome determinant model for providing healthcare, comprising:

creating a best practices model in the form of a best practices database interfacing with a processor device incorporating a software based algorithmic medium, the model presenting a series of treatment options ranging from desirable to undesirable associated with a given type of service;

establishing a decision support system interfacing with the best practices database and processor device, the support system providing any of a grading or awarding system for scoring, in real time, performance metrics for each of any number of providers of the service;

outputting to a plurality of subset devices associated with each of a plurality of service providers real time and continuously updated scoring of performance metrics based upon the grading or awarding system and as a result of the treatment options selected and inputted by the providers;

incentivizing adherence by the providers to the best practices model by tying desirable performance metrics to financial incentives which are scaled to each treatment option;

designating a sum of funds representative of an operating budget for a service provider and for disbursement on a percentage basis to each of any number of subset service providers based upon adherence to the best practices model; and subdividing said sum between different practice groups and sub-specialties associated with a given class of service providers.

10. The method of claim 9, further comprising providing and incentivizing a patient input function to the processor driven device as medical data input, biographical data input, commentary regarding the service provider, or a rating regarding a service provider.

11. The method of claim 9, further comprising incorporating a management module having at least one additional subroutine interfacing with the processor driven device for monitoring and tracking adherence to the best practices model.

12. The method of claim 9, further comprising designating a sum of funds representative of an operating budget for a service provider and for disbursement on a percentage basis to each of any number of subset service providers based upon adherence to the best practices model.

13. The method of claim 12, further comprising subdividing the sum between different practice groups and sub-specialties associated with a given class of service providers.

14. The non-transitory software based algorithmic medium of claim 1, further comprising a comparison metric for providers to measure their performance versus other providers within a group and providers in other groups.

15. The non-transitory software based algorithmic medium of claim 1, further comprising creation and management of an editable specialty physicians providers network.

16. The non-transitory software based algorithmic medium of claim 1, further comprising distribution of shared savings and other financial incentives between patients, providers and payers.

17. The non-transitory software based algorithmic medium of claim 1, further comprising real-time feedback for providers compliance with best practice on every patient enrolled in a program.

\* \* \* \* \*